United States Patent [19]

Berta

[11] Patent Number: 5,314,537
[45] Date of Patent: May 24, 1994

[54] GELATIN COATED CAPLETS AND PROCESS FOR MAKING SAME

[75] Inventor: Norbert I. Berta, Radnor, Pa.

[73] Assignee: McNeilab, Inc., Spring House, Pa.

[21] Appl. No.: 190,616

[22] Filed: May 5, 1988

Related U.S. Application Data

[62] Division of Ser. No. 16,914, Feb. 20, 1987, Pat. No. 4,820,524.

[51] Int. Cl.$^5$ .................................. B05C 03/09
[52] U.S. Cl. ........................... 118/30; 118/16; 118/20; 118/423; 118/425; 118/428; 118/500; 118/503
[58] Field of Search ............ 427/3; 118/500, 503, 118/30, 16, 20, 423, 425, 428, 13, 18, 56, 66, 107, 416

[56] References Cited

U.S. PATENT DOCUMENTS

| | | | |
|---|---|---|---|
| 599,865 | 3/1898 | Richards | 118/30 X |
| 671,804 | 4/1901 | Metcalf | 424/478 |
| 724,436 | 4/1903 | Clark | 118/30 X |
| 1,872,190 | 8/1932 | Sindl | 425/272 |
| 2,868,158 | 1/1959 | Hilliard | 118/30 |
| 3,045,641 | 7/1962 | Oddo | 118/16 |
| 3,185,626 | 5/1965 | Baker | 167/82 |
| 3,228,789 | 1/1966 | Glassman | 117/118 |
| 3,736,152 | 5/1973 | Turner | 118/30 |
| 3,844,818 | 10/1974 | Morrison | 118/503 X |
| 3,856,498 | 12/1974 | Campagna et al. | 118/503 X |
| 3,896,762 | 7/1975 | Banker | 118/30 |
| 3,921,575 | 11/1975 | Ishii et al. | 118/503 X |
| 4,050,407 | 9/1977 | Garwood et al. | 118/503 X |
| 4,171,041 | 10/1979 | Lowe | 118/503 X |
| 4,238,510 | 12/1980 | Cherukuri | 426/5 |

FOREIGN PATENT DOCUMENTS 52-041213  3/1977  Japan .
60-084215  5/1985  Japan .

OTHER PUBLICATIONS

*Remington's Practice of Pharmcy*, Martin & Cook, 17th Ed., pp. 1625-1630.
Cherry-Burrell Trade Literature for 950 Hard Gelatin Capsule Machine, Cedar Rapids, IA.
Vector/Freund Trade Literature for Hi-Coaters System, Marion, IA.
C. G. Richardson, Franciscus Pill Coater, Int'l. Pharm. Abs., 28:90-91, pp. 70-86 (Oct. 1986).(abstract).
Stedman's Medical Dictionary, Anderson Publ. Co., 5th ed., Williams and Wilkins Baltimore, MD (1982) p. 1377.
Lackman, *The Theory and Practice of Industrial Pharmacy*, Liberman and King, pp. 389-398 (1970).
Glatt Air Techniques Trade Literature for GC-1000, Ramsey, N.J.

*Primary Examiner*—Thurman K. Page
*Assistant Examiner*—Neil Levy
*Attorney, Agent, or Firm*—Joseph F. Shirtz

[57] ABSTRACT

A capsule-like medicament, method for producing such medicaments and apparatus. Such medicaments are achieved by individually dipping and drying first one end, and then the other end, of each caplet to provide a coating which is another and easier to swallow than an uncoated caplet. The production of these capsule-like medicaments is readily facilitated by simple and inexpensive modifications which can be made to existing empty gelatin capsule making equipment.

23 Claims, 5 Drawing Sheets

GELATIN COATED CAPLETS AND PROCESS FOR MAKING SAME

This is a division of application Ser. No. 016,914, filed Feb. 20, 1987, now U.S. Pat. No. 4,820,524.

FIELD OF THE INVENTION

This invention relates to coated medicaments and processes for providing gelatinous coverings for such medicaments. This invention is also directed to novel apparatus for producing such medicaments.

BACKGROUND OF THE INVENTION

Until recently, the pharmaceutical industry has relied upon empty gelatin capsules for the encapsulation of medicinal agents as a popular method for administering drugs. Hard capsules are not new. As early as 1848, Murdock introduced the two-piece, hard gelatin capsule. Capsules are tasteless, easily administered and easily filled either extemporaneously or in large quantities commercially. Many patients find it easier to swallow capsules than tablets, therefore preferring to take this form whenever possible. This preference has prompted pharmaceutical manufacturers to market certain products in capsule form even though they are also available in tablet form.

Empty gelatin capsules are typically made from gelatin-glycerin, pure gelatin, starch or sugar gelatin, or other soluble gelatin combinations. See *Remington's Practice of Pharmacy*, Martin & Cook, 17th edition, pp. 1625–1630, which is herein incorporated by reference. Capsules serve as adequate housings for powders, masses, liquids, pellets and oils and offer improved palatability and convenience.

Generally, empty hard gelatin capsules are manufactured using automated equipment. This equipment employs rows of stainless steel pins, mounted on bars or plates, which are dipped into a gelatin solution maintained at a uniform temperature and fluidity. The pins are then withdrawn from the gelatin solution, are rotated and then inserted into drying kilns through which a strong blast of filtered air with controlled humidity is forced. A crude capsule half is thus formed over each pin during drying. Each capsule half is then stripped, trimmed to uniform length, filled and joined to an appropriate mating half. Such hard capsule making systems are sold by Cherry-Burrell of Cedar Rapids, Iowa.

During most of this century, empty gelatin capsules were a popular dosage form for prescription and over-the-counter (OTC) drugs. However, in the early 1980's there was an unexpected increase in tampering with the contents of those capsules, resulting in several widely publicized deaths. This curtailed consumer demand for these products, caused ubiquitous concern regarding safety among those in the pharmaceutical community, and idled much of the industry's hard capsule making equipment. Improved gelatin capsules and tamper-resistant packaging were then developed, but were expensive to produce and were not foolproof.

Once the threat of capsule tampering was recognized, many manufacturers withdrew their capsule products from the market, often replacing them with solid, oblong-shaped medicaments referred to commonly as caplets. Caplets are solid oblong tablets which are sometimes coated with material such as cellulose. Typically, this coating is applied using coating-pan systems such as the "Vector-Freund Hi-Coaters", sold by Vector Corporation, 675 44th Street, Marion, Iowa, or the "GC-1000" sold by Glatt Air Techniques, 20 Spear Road, Ramsey, N.J.

A coating-pan system has a perforated pan or a drum which revolves in a manner similar to a standard clothes dryer. The system includes an air-atomization, spray gun which is inserted into the center of the drum for spraying a fine mist of coating material. A batch of solid medicaments or caplets is typically introduced into the cylindrical pan, wherein said batch is caused to tumble. The tumbling action tends to smooth out some of the rough edges on the caplets prior to coating with organic or aqueous film solutions which may contain solid additives. Coating pans generally produce consistent coating thicknesses and weights but are capable of providing only one color coating. Coatings produced by this method are often thin, offering poor coverage of medicament imperfections and rough edges not removed by the tumbling operation. Unless time is taken to build up a thicker coat, defects on the solid core result in a medicament that does not exhibit a pleasing appearance and may be perceived as being harder to swallow. Moreover, coating abrasion occurring during tumbling produces a surface finish on these medicaments that fails to exhibit the shiny surface that consumers and those in the art have associated with ease of swallowability. Applicant has pan coated caplets with gelatin on an experimental basis and has measured coating thicknesses of only about 6 mils. Moreover, these pan coated gelatin caplets were not observed to be as shiny as caplets coated by a dipping process.

Swallowability, the ability to pass through the fauces, pharnyx and esophagus into the stomach, is dependent on the physical characteristics of the medicament as well as psychological factors. See *Stedman's Medical Dictionary*, Anderson Publishing Co., 5th edition, p.1377, which page is herein incorporated by reference. Physical characteristics, such as medicament shape, size and surface finish, can be correlated with esophageal adherence and swallowability. With respect to psychological factors, swallowing is normally volitional in adults, and muscular contractions of the throat are understood to be under the control of the individual at a subconscious level. See *Stedman's*, at 1377. Consumer surveys suggest that a shiny, capsule-like appearance has a special appeal to users as being easier to swallow. In addition, surveys indicate that consumers perceive capsule products to be more effective, thereby adding a possible additional placebo factor to their actual effectiveness.

Solid medicaments comprising gelatin in their coatings have been taught in a number of abstracts. The abstract of J. A. Glassman, U.S. Pat. No. 3,228,786, for instance, is directed to peroral capsules and tablets and a method for manufacturing same. Glassman discloses delayed release, compartmental medicaments with gelatin coatings, and includes treatments for tablets or pellet coatings. The abstract of Japanese patent 52041213, assigned to Freund Industry Ltd., discloses a process for coating tablets with a solution containing gelatin as a film-forming agent. The abstract of Japanese patent 69027916, assigned to Sankyo Co. Ltd., is directed to gelatin coated tablets and a process for making same. The process of this patent includes feeding raw tablets at continuous intervals into a support. The tablets are immersed in a coating solution which can comprise gelatin. They are then recovered and held on a holder. Excess coating solution deposited at the lower surface of the tablet is removed by an eliminating plate, and finally the tablet is released into a cooling solution from which it is recovered and dried to produce a *seamless* coated tablet. The abstract of Japanese patent 65009992, assigned to Konishi, is directed to a film-coating method using gelatin for coating tablets in a coating pan. The gelatin described in this abstract is pre-treated with water in a pressure-cooker at a 120°-140° F. for 30-40 minutes to reduce the adhesive properties of the gelatin to allow coating of the tablet. The abstract of Japanese patent 65009994, also assigned to Konishi, is directed to coating tablets in a coating pan with an emulsion including a mixture of hot water, gelatin, a surface active agent and a member selected from a group consisting of fats and oils, paraffin and wax. The use of the emulsion described in this patent abstract allows tablets to be coated with gelatin in the same manner as coating tablets with sugar. See also the abstract of an article by Richardson entitled "Franciscus Pill Coater", *Pharm. Hist.*, 28: 90-91 (2)1986. This abstract is directed to the Franciscus Pill Coater, one of the later refinements of the gelatin-coated process that appealed to the practicing pharmacists in the 19th century. Other abstracts also disclosing coatings for solid medicaments comprising gelatin Chemical Industries, U.S. Pat. No. 4,238,510, assigned to Lifesavers, Inc., and Japanese patent 69026677, assigned to Daiichi Seiyaku Co. Ltd.

Several patents have disclosed the concept of coating pills by dipping half the surface of the pill at a time. Richards, U.S. Pat. No. 599,865 is directed to a process and apparatus for dipping pills wherein an adhesive bearing bar is used to hold the pills before dipping them into gelatin. This process requires great care in maintaining the consistency of the adhesive material, i.e. wax, so that each pill will adhere to the dipping-bar. The specification of Richards also warns that great care must be taken not to dip the pills so deep as to get any of the gelatin upon the wax, which may ruin its adhesive capacity. The method of Richards additionally is labor intensive, and therefore, is more expensive by today's standards. Clark, U.S. Pat. No. 724,436, is directed to a pill coating machine that employs pill-bars having a series of perforations for receiving pills. Each perforation is adapted for suction, whereby the pill is held in position during the dipping operation. Banker, U.S. Pat. No. 3,896,762, discloses a rotary immersion coating that similarly employs suction to hold solid medicaments prior to passing these medicaments through a coating bath. While Clark and Banker provide apparatus for holding and dipping medicaments, neither discloses that the final product will exhibit a capsule-like appearance with or without a seam. Moreover, applicant has tested vacuum holding apparatus and has discovered that the suction tends to attract some of the gelatin into the holder, producing an irregular seam. Vacuum holding systems such as these also require significant power consumption, are often complicated and uncertain in their action, and necessitate expensive and sensitive vacuum equipment. Finally Oddo, U.S. Pat. No. 3,045,641, discloses apparatus for color-coding tablets that utilizes a rotating resilient roller impregnated with a coating substance, whereby tablets are passed beneath the roller on a conveyor and are deeply impressed into the resilient roller surface. This patent does not disclose the use of gelatin or the use of a dipping process to produce a thick capsule-like coating.

Although these gelatin coated medicaments and processes have achieved some commercial success in the marketplace, a need remains for a coated medicament which is at least as tamper-resistant as a caplet while providing the ease of swallowability of a capsule. There is also a need for a less expensive medicament coating method capable of producing a multi-colored, capsule-like coating which is perceived by the consuming public to be more effective.

SUMMARY OF THE INVENTION

The present invention provides a novel method for coating solid cores, such as caplets, with gelatinous coatings to produce simulated capsule-like medicaments. Such capsule-like medicaments are achieved by individually dipping and drawing first one end and then the other end of each caplet to provide a medicament which is observed to be similar to a regular capsule. The production of such capsules is readily facilitated by simple and inexpensive modifications which may be made to existing, hard capsule, production equipment or by similarly designed newer equipment. In particular, the preferred apparatus of the present invention replaces the prior art steel pins of a standard capsule production machine with novel caplet holding means having caplet channels therein for receiving, individually gripping and transferring caplets during various stages of the herein described coating process. Also included, are novel caplet designs which readily facilitate the method of this invention. As a result, novel capsule-like medicaments are provided having smooth, relatively thick, shiny, multi-colored gelatinous coatings thereon. These medicaments are pleasing to the eye, and should be perceived by consumers as easier to swallow and more effective than prior art caplet medicaments, while providing much greater tamper resistance than conventional capsules.

It is, therefore, an object of this invention to provide a simulated, capsule-like medicament having a gelatinous coating capable of being provided in two or more colors.

It is another object of this invention to provide a simulated, capsule-like medicament that is tamper-resistant.

It is another object of this invention to provide a simulated, capsule-like medicament that provides greater ease in swallowing and is perceived to be more effective than pan-coated pharmaceutical equivalents.

It is still another object of this invention to provide a novel and less expensive method and apparatus for adapting existing hard capsule equipment for manufacturing gelatin coated caplets.

It is still another object of this invention to provide a heavy layer of gelatin as a single coating to cover imperfections inherent on the caplet core.

With these and other objects in view, which will become apparent to one skilled in the art as the description proceeds, this invention resides in the novel construction, combination, arrangements of parts and methods substantially as hereinafter described and more particularly defined by the attached claims.

BRIEF DESCRIPTION OF THE DRAWINGS

The accompanying drawings illustrate a complete embodiment of the invention according to the best mode so far devised for the practical application of the principles thereof, and in which:

FIG. 8a–d are enlarged details of transverse views of caplets illustrating various coating patterns.

FIGS. 11(a) and (b) are enlarged details of the longitudinal cross-section views of the alternative holding means of FIG. 1B showing how the ends of the caplet are held.

DETAILED DESCRIPTION OF THE INVENTION

The present invention provides a novel method for coating caplets with gelatinous coatings to produce simulated capsule-like medicaments. The subject method may be performed by modifying existing machines originally intended to fabricate empty gelatin capsules or by newer similarly designed apparatus.

The novel process of this invention comprises the steps of providing a holding means having a caplet channel defined therein and inserting a first end of a caplet into said caplet channel while leaving the second end of the caplet exposed. The holding means is then manipulated relative to a bath of gelatinous coating to dip the second exposed end of each caplet into that bath. The resulting gelatinous coating on the second exposed end of the caplet is then permitted, and preferably caused, to dry to form a coated end. During the drying process the caplet may be rotated to assist in uniformly distributing gelatin during drying. Once dry, the coated (second) end of the caplet is then displaced through the caplet channel to expose its uncoated first end. A gelatinous coating is then applied to the uncoated first end of said caplet. The coating applied to the first end of the caplet is then permitted (or preferably caused) to dry, again with rotation if desired for the purpose of spreading the coating evenly. In accordance with the preferred embodiment method, the baths of gelatinous coating into which the caplet ends are dipped may be of different colors, to thereby create a simulated 2-piece capsule look to the finished caplets with seams about their transverse axes.

A substantial advantage of the present invention is that existing hard capsule manufacturing may be readily adapted for the purpose of producing the coated caplet products of the present invention. In the preferred embodiment apparatus of the present invention, the conventional bars of such machines having stainless steel capsule-forming protuberances mounted thereon are replaced with bars having a plurality of cylindrical holding means mounted thereon. Each holding means receives, retains and facilitates the transfer of an individual caplet. The apparatus is fitted with a caplet feeder to feed caplets into each holding means. The holding means may, for example, be a cylinder which is open at both ends and which comprises a retaining means, such as "O"-rings or a spring biased retainer for the purpose of holding each caplet in position during the dipping process. The feeding means is preferably associated with an inserting means, which may be a simple channel and plunger assembly, for inserting a first end of each caplet into an appropriate holding means. The feeding means ensures that each caplet is inserted a sufficient distance to cause the second end of the caplet to appropriately protrude therefrom during the upcoming dipping process. Once each bar is loaded with caplets, it then proceeds to a dip station where the gelatinous coating is applied to the exposed ends of the caplets protruding therefrom, whereupon the bar is rotated through a first drying means for permitting the gelatinous coating to dry to form a coated second end. In a preferred embodiment apparatus, the second gripping means also comprise substantially cylindrical holders which are open at both ends, having central bores defined therethrough. In this embodiment, these second holders are axially aligned with the bores of the first holders, at the transfer positions, whereupon a plunger or other means is used to displace the half-coated caplets through and out of the "backs" of the first holders and into the "backs" of the second holders, and then through the second holders until the remaining uncoated ends of the caplets are exposed for subsequent dipping. The dipping and drying processes are then repeated (preferably with a different colored gelatinous coating), whereupon a caplet ejection means pushes the caplets out of the second holders.

In another preferred embodiment, the "fronts" of the second holder means are aligned with the "fronts" of the first holder means, whereupon the caplets are mechanically transferred from the first to the second holders without the need for an additional alignment device. In still another embodiment, a single holding means is used for dipping both ends of the caplet, whereby, after dipping the second end, the caplet is transferred through this single holding means to expose the uncoated first end. This holder is then shifted to the second gelatinous coating bath which preferably contains a different color gelatin for dipping the first end of the caplet.

Figure 1:
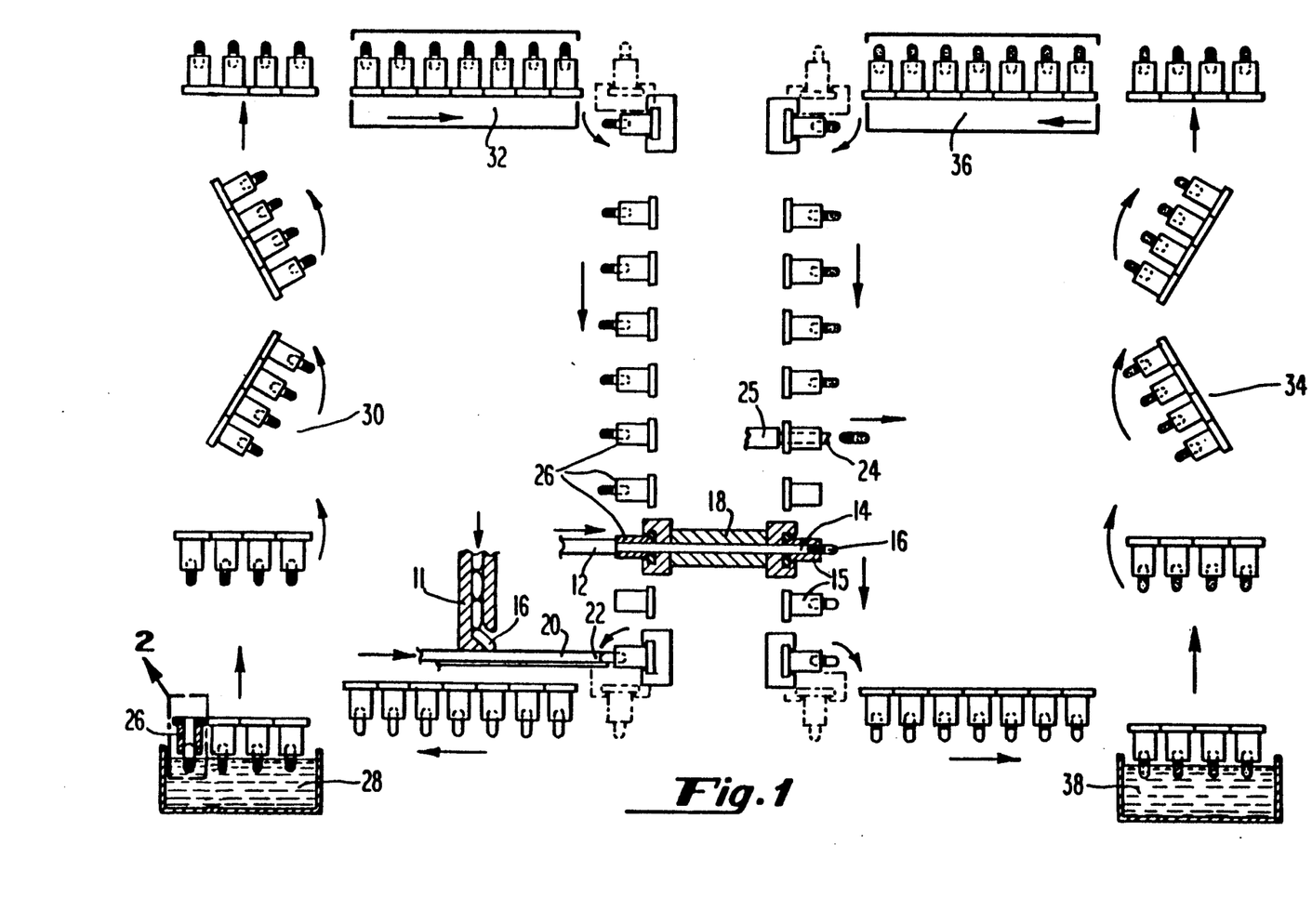
FIG. 1 is a diagrammatic view of the manufacturing sequence for providing a gelatin coating on caplets illustrating how the caplets are inserted, how the gelatinous coating is applied to the first and second ends of the caplet, and how the caplets are dried and ejected.
Figure 2:
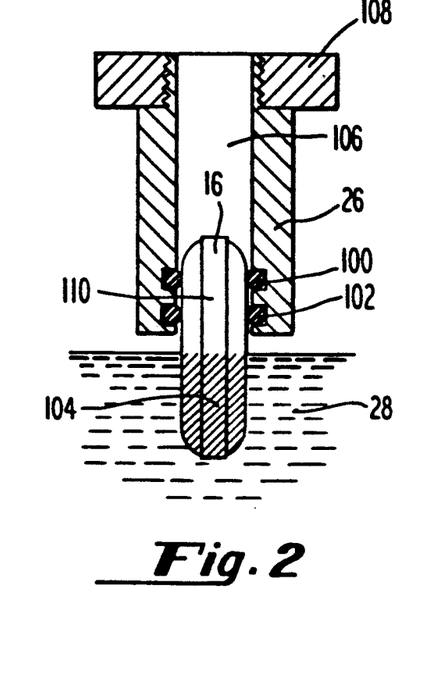
FIG. 2 is an enlarged detail of a cross-sectional view of the holding means 26 of FIG. 1 with a caplet being dipped in a gelatinous material, said caplet being retained by "O"-rings 100 and 102.

The subject apparatus and method may be further understood with reference to the figures. FIG. 1 illustrates, diagrammatically, the preferred method and apparatus for dipping solid caplets into a gelatinous material embodying the teachings of this invention. A holding means is first provided having a caplet channel 106 defined therein (see FIG. 2), which can take any form having a cross-section sized to slidably mate with said caplet 16. The caplet 16 having a first and second end, 110 and 104 of FIG. 2, is inserted using inserting means 20 (see FIG. 1) into said caplet channel 106 while leaving the second end of the caplet 104 exposed. Next, a gelatinous coating, known to those in the pharmaceutical arts, is applied by first application means 28 to the exposed second end 104 of the caplet. The extent to which the second end 104 can be coated is dependant upon the desired color configuration and "seam" requirements. The half-coated caplet is then dried using the first drying means 30 and 32 which permits the gelatinous coating on the second end 104 to dry, forming a coated second end. The caplet 16 is then displaced through said caplet channel 106 to expose the first end 110 preferably using a gripping means illustrated in the embodiment of FIG. 1 as transfer means 12, alignment means 18 and second holding means 15. The caplet 16 is then coated with a gelatinous material on its first end 110 by second application means 38 which is then dried by second drying means 34 and 36, resulting in a dry caplet substantially covered in gelatin. Accordingly, this invention provides novel means for providing simple and inexpensive modifications to existing hard capsule equipment to manufacture simulated capsule-like medicaments. This invention teaches preferred process sequences that supplement and partially replace otherwise standard empty gelatin capsule techniques and parameters that are known to the art. For example, gelatin materials used for the coatings of this invention may be any of the well known types utilized in the art of manufacturing empty capsules and coated medicaments.

Referring again to FIG. 1, the caplet 16 is fed into inserting means 20 by feeder 11. The feeder 11 preferably comprises a chute attached to a reservoir. Alternatively, mechanical means or pneumatic means may be developed for this purpose. In one embodiment, a 20–40 wide channel vibrational feeder has been deemed useful. It is expected that those in the art could readily adapt current automation technology to develop a means for feeding caplets into inserting means 20 of this invention. In the preferred embodiments, plungers displace caplets into each of a series of molding means spaced apart along a bar mount, shown in end cross section in FIG. 1, i.e., holding means 26. Each caplet 16 is then inserted into a first holding means 26 using plunger 20. Both the first and second holding means 26 and 15 are preferably cylindrical, having caplet channels 106 having a cross-section sized to slidably mate with the caplet 16 to permit passage of the caplet 16. However, in the embodiment of FIG. 1A, these channels, or more preferably, bores, can extend through the holding means with one cross-section sized to slidably mate with caplet and another cross-section sized to receive only a plunging means. This design is made possible due to the fact that the caplets can be transferred without displacing them through the entire length of the holding means in the method embodiment of FIG. 1A.

Figure 3:
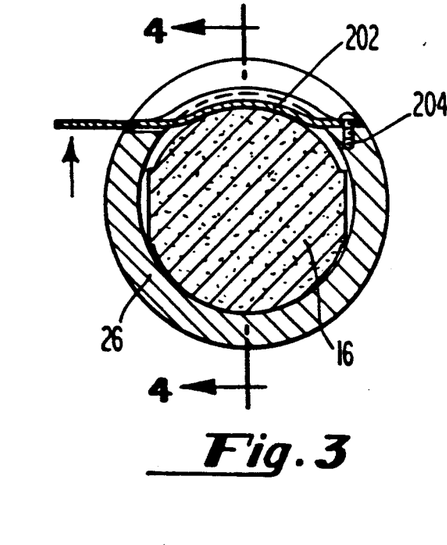
FIG. 3 is an enlarged detail of a transverse cross-sectional view of an alternate holding means illustrating a flat spring 202.
Figure 4:
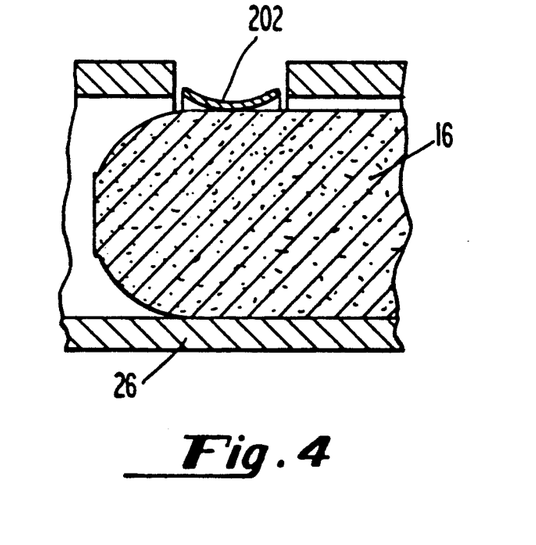
FIG. 4 is an enlarged detail of a longitudinal cross-sectional view of a caplet being retained by flat spring 202 of FIG. 3, taken through line 4—4.
Figure 5:
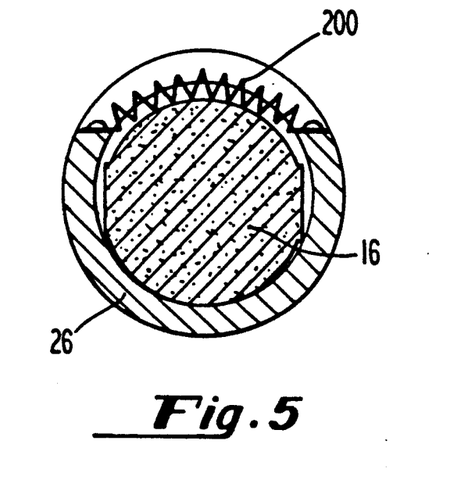
FIG. 5 is an enlarged detail of a transverse cross-sectional view of an alternative holding means embodiment illustrating a spring retention means 200.

Included with one holding means embodiment of this invention, are retaining means for retaining the caplet at least during the first gelatinous coating application step. As shown by the embodiments found in FIGS. 2-5, the retaining means can comprise a plurality of recessed rubber "O"-rings 100 and 102, a flat spring 202 fixed by pin 204 and having convex side facing the caplet, or a resilient spring 200. As shown in FIG. 3 the flat spring 202 may be extended to enable external manipulation of the retaining means. The choice of retaining means is not critical and any known securing or resilient device may be used. However, it is important that the retaining means provide enough clearance to pass the gelatin coated end, yet securely hold the uncoated end.

Inserting means 20 preferably comprises a plunging means having at least an end portions 22 disposed to abut the caplet 16 to effect displacement of the caplet 16 into the bore 106 of the first holding means 26.

In a preferred embodiment, a plurality of holding means are mounted on a fixture which can be transferred by the mechanical pushing means of a hard gelatin capsule assembly line. In such an embodiment, inserting means 20 has multiple plunging means having a plurality of end portions 22 disposed to abut multiple caplets to effect displacement thereof into the fixture. In one embodiment, 10 to 50 holding means, preferably 20 to 40, and most preferably 30 holding means are attached to the fixture. A plurality of said fixtures can be fed into a conventional hard-capsule manufacturing assembly which can accommodate about 1500 to 1800 fixtures at a time.

The caplet coating process of FIG. 1 next applies a gelatinous coating to the second exposed end 104 of said caplet 16. A first application means 28 is employed for this purpose. In the preferred embodiment of this invention, groups of 4 or more fixtures are fed into a dipping means and vertically lowered into a gelatinous material such as methyl cellulose, calcium alginate or gelatin. The depth of the dip is preferably cam-regulated to the desired capsule size, color scheme, and "seam" requirements. As indicated in FIG. 8a–d, the color scheme can be bifurcated as depicted by caplet coatings 304 and 306, and a seam 302 or 300 can be provided by overlapping the gelatinous coatings on the first and second ends 110 and 104.

The coatings on the first and second ends 110 and 104 of the caplet, when preferably dipped in gelatin can include plasticizers such as glycerin or sorbitol, water, preservatives, coloring agents, and opacifying agents. See *Remington's Practice of Pharmacy*, pages 1625 to 1630. The preferred gelatin solution should be maintained at a uniform temperature and a constant degree of fluidity. If the gelatin solution varies in viscosity, it will correspondingly decrease or increase the thickness of the coating. Acceptable gelatin compositions can contain small amounts of methyl cellulose, polyvinyl alcohols, and denatured gelatins to modify their solubility or produce a enteric effect. Common sources of gelatin contemplated by this invention include animal bones, hide portions and frozen pork skin. Grades of gelatin that are appropriate for this invention include pharmaceutical grade, food grade, Type A and Type B. Although the coatings herein provided can be made from any of these sources or grades, those learned in the art of capsule making are aware that the usual practice is to use a mixture of grades and sources as dictated by availability and cost considerations. Differences in the physical properties of finished capsules as a function of the type of gelatin used are slight. Reference may also be made to "The Theory and Practice of Industrial Pharmacy, by Lackman, Liberman and King (1970) pages 389-398, published by Lea and Febiger, Philadelphia, Pa., said pages being hereby incorporated by reference. In a preferred embodiment of this invention, a gelatin mixture is prepared using 40% by weight bone (150 bloom), 20% by weight hyde (245 bloom) and 40% pork skin (270 bloom). This mixture has a viscosity of 500 cp as measured on a Brookfield Chromatograph, at an operating temperature of 130° F.

Coloring can be added to the coatings to produce opaque or transparent colors such as red, white, pink, green, reddish brown, blue, yellow and black. Colored medicaments are necessary to give a specialty product a distinctive appearance. Titanium dioxide is often added to the gelatin to form white medicaments, or to make an opaque colored coating.

Still referring to FIG. 1, after coating the second end 104, the gelatinous coating is permitted to dry to form a coated second end. It is important to the teachings of this invention that the caplet 16 is permitted to dry without contacting other objects, thus producing a shiny, simulated capsule-like finish on said caplet. In the preferred embodiment, a group of fixtures is raised from the gelatin and elevated to the first drying means, comprising rotating means 30 and kiln means 32. Preferably, the caplets are rotated to distribute the coating on the caplet. In a most preferred apparatus, the fixtures are automatically revolved after dipping to spread the gelatin more evenly over the caplet ends and eliminate excess accrual at the ends. See Sindl, U.S. Pat. No. 1,872,190, which is herein incorporated by reference. The caplets are then fed into a kiln drying means 32. Preferably, 5-60 fixtures containing caplets enter the drying kiln, where they move under drying ducts. Air volume, temperature and humidity are controlled in the kiln and are set to conventional process parameters known to those in the industry.

When the gelatinous coating on the second end 104 of the caplet is dry, it is displaced through the caplet channel 106 to expose the first end 110 using a gripping means illustrated in the embodiment of FIG. 1 as transfer means 12, alignment means 18 and second holding means 15. In one preferred embodiment, the transfer means 12 comprises an end portion 14 disposed to abut said caplet to effect displacement of said caplet from a the first holding means 26 to the second holding means 15. The caplet is then preferably displaced through the caplet channel or bore 106 of the first holding means 26, through the alignment means 18 and into said second holding means 15 to expose the uncoated first end 110 of the caplet 16.

Figure 1A:
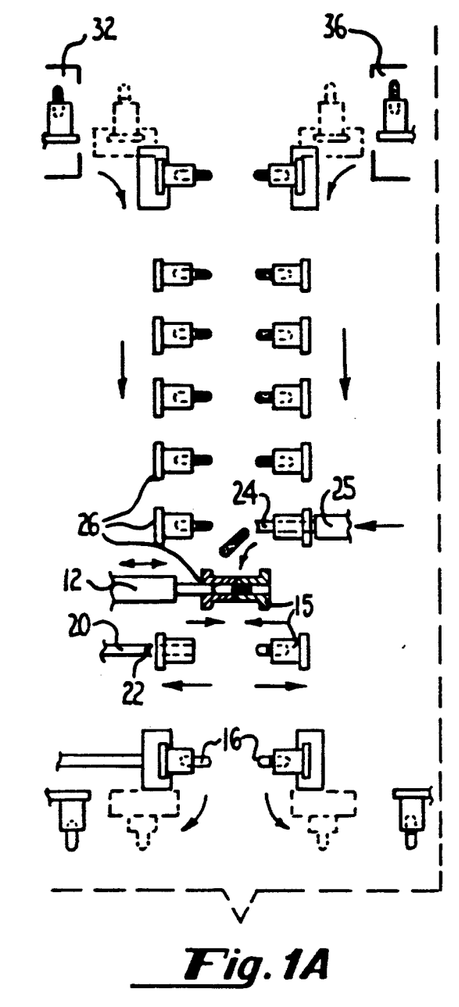
FIG. 1A is a partial diagrammatic view of an alternative manufacturing sequence illustrating an alternative transferring method.
Figure 1B:
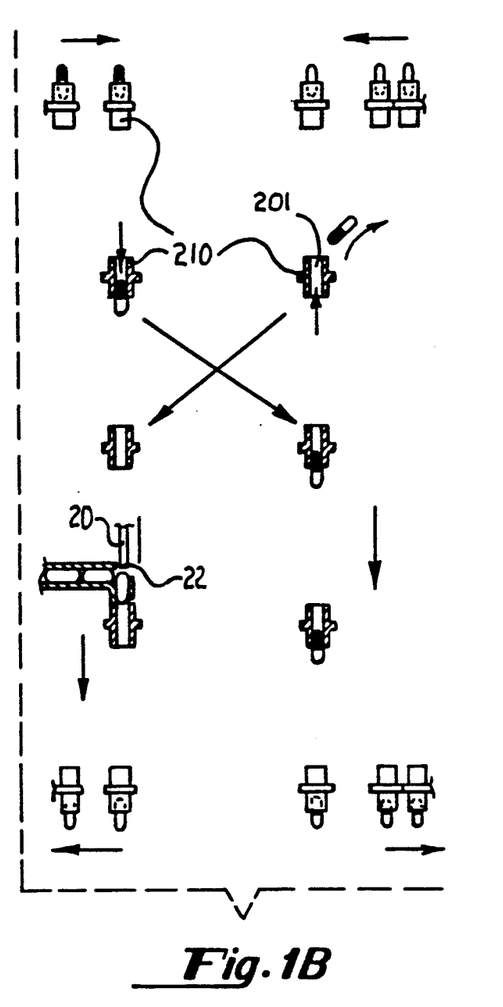
FIG. 1B is a partial diagrammatic view of an alternative manufacturing sequence illustrating an alternative holding means and transferring method.
Figure 11:
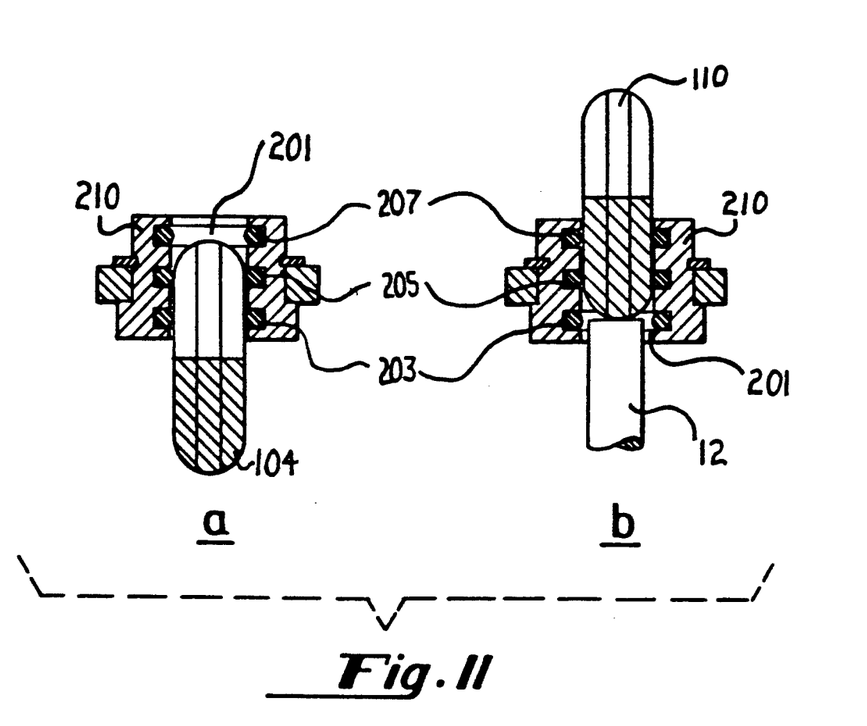

Alternatively, as depicted in FIG. 1A, when the gelatinous coating on the second end 104 is dry, it can be displaced through the caplet channel 106 to expose the first end 110 by transferring the caplet from the "front" of a first holding means to the "front" of a second holding means, thus eliminating the need for alignment means 18 of FIG. 1. It is also envisioned that a single holding means 210 like the one illustrated in FIG. 11(a) and (b) could replace the use of the two holding means 26 and 15 of FIGS. 1 and 1A by providing for the displacement of the caplet through a central bore 201. Three "O"-rings 203, 205 and 207 are shown in FIGS. 11(a) and (b) for retaining the caplet during the process of coating the second and first ends 104 and 110 using a single holding means 210. However, other retaining means, as previously described for the holding means 26 and 15 of FIG. 1, may also be employed for this purpose. As illustrated, in the embodiment of FIG. 1B, by transferring bars containing a plurality of holding means 210 from the left side of the diagrammatic view of the process of FIG. 1 to the right side, the need for a second holding means is eliminated.

Figures 6, 7, 8:
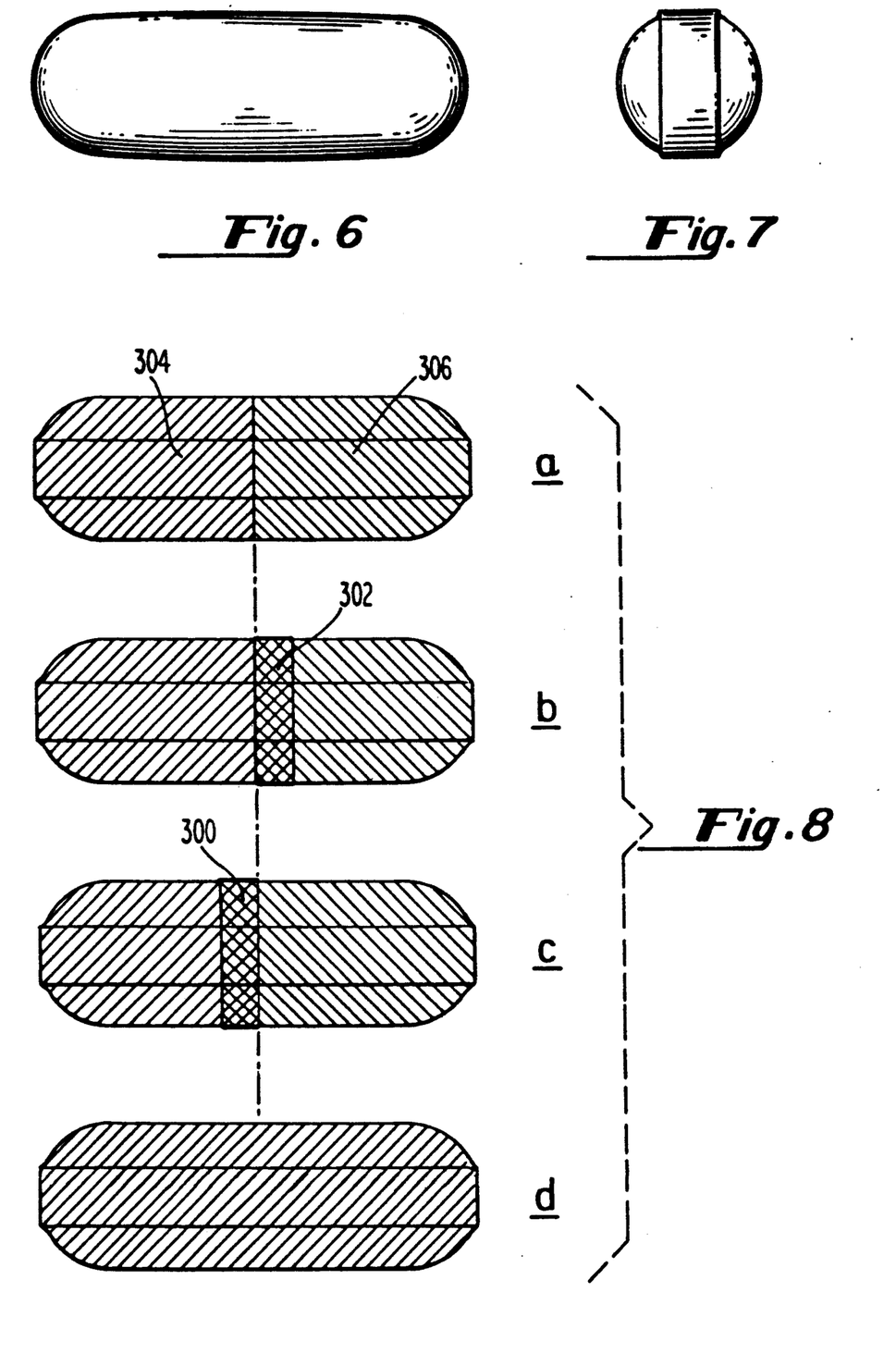
FIG. 6 is an enlarged top view of an uncoated caplet.
FIG. 7 is an enlarged detail of a transverse view of the caplet of FIG. 6.

After displacing the caplet through the caplet channel 106, the protruding first end is ready for the application of a gelatinous coating which is illustrated on the right side of FIG. 1. As indicated in the above preferred embodiments, groups of 4 or more fixtures can be fed into a dipping means 38 and vertically lowered into a gelatinous material, preferably containing a different color dye or pigment for providing a distinctive appearance. As indicated in FIG. 8, a seam 300 or 302 can now be provided by overlapping the dried coating on the second end 104. Through careful selection of gelatin color schemes, the seam can exhibit a different color than the ends of the caplet, i.e., green and yellow coatings on the ends can be overlapped to form a blue seam. The gelatinous coating on the first end is then permitted to dry without contacting other objects, as previously described for the second end 104. Separate rotating means 34 and kiln means 36 are illustrated in FIG. 1 for drying the coating on the first end. However, those in the art may find it convenient to use the same drying apparatus used in drying the second end 104.

Finally, the caplet may be ejected from the second holder means 15 after the first end 110 is dry. Removal of the coated caplet 16 can be effected by ejection means 25 which preferably is similar in structure to inserting means 20 and transfer means 12, in that it comprises an end portion disposed to abut said caplet. Removing the caplet can be accomplished by plunging horizontally as in FIGS. 1 and 1A or by plunging the caplet out of the holding means vertically as in FIG. 1B. The ejected caplet, now coated in gelatinous material, is then ready for printing and packaging.

In view of the above it is expected that a novel, simulated capsule-like medicament can be produced. The gelatin coated medicament of this invention which can be produced by the above method comprises a solid caplet having a first and a second end, wherein a first gelatinous coating is provided on said second end, and a second gelatinous coating is provided on said first end of the caplet. The caplet generally is at least 2.5 times longer than it is wide, and ideally comprises a cylindrical shape. The first and second gelatinous coatings substantially cover the caplet to form a simulated capsule-like medicament with a seam about a transverse axis of the medicament. As previously discussed, the first and second ends 110 and 104 of the caplet can be coated with gelatinous coatings of different colors to provide a distinctive appearance for specialty products. A preferred color scheme for the medicament of this invention includes a caplet which is coated in a red and white gelatinous material. It has been discovered that absorption of the gelatinous coating or the . moisture in the gelatinous coating by the solid caplet may be reduced by applying a conventional precoat sealant to caplet prior to dipping into a gelatinous material. See Baker, U.S. Pat. No. 3,185,626, which is herein incorporated by reference. Without a precoat sealant, it is possible that some of the gelatinous coating or moisture in the coating would seep into the caplet, resulting in a duller surface. The gelatinous coatings of this invention are generally provided in substantially uniform thicknesses of about 5 to 40 mils, preferably about 10 to 30 mils, and most preferably from 15 to 25 mils. However, it may be understood by those familiar with coating processes that the coating thickness may be varied to provide a smoother, easier to swallow, caplet.

Gelatin coated caplets have been produced using the above method, wherein the second applied gelatinous coating partially overlaps the first applied gelatinous coating forming a capsule-like seam circumscribing the medicament at about a midway point of a longitudinal access of the medicament.

Figure 9:
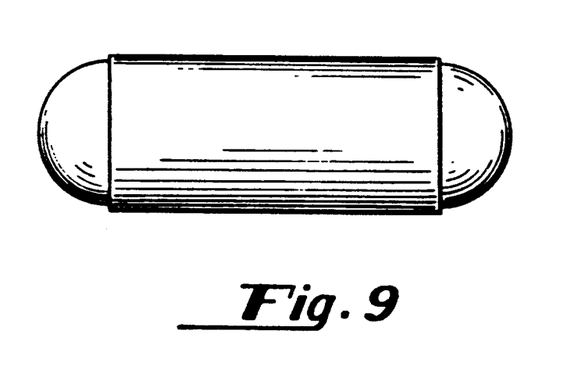
FIG. 9 is an enlarged longitudinal view of an alternative shape for an uncoated caplet.
Figure 10:
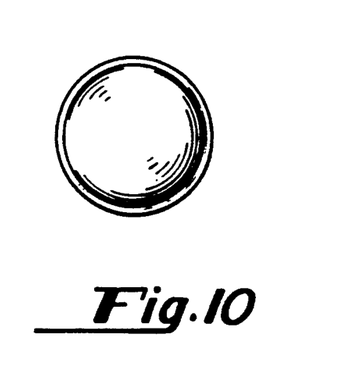
FIG. 10 is an enlarged detail of a transverse view of the caplet of FIG. 9.

Gelatin coated caplets can be supplied in a variety of shapes and sizes, from 000, the largest size which can be swallowed, to 5, which is the smallest. Larger sizes can also be made available for use in veterinary medicine. FIGS. 6, 7, 9 and 10 illustrate two of the preferred shapes for caplets. FIGS. 6 and 7, show in top and transverse views respectively, an oblong caplet having a raised portion circumscribing its perimeter. FIGS. 9 and 10 illustrate in longitudinal and transverse views another preferred embodiment having a cylindrical center portion and rounded ends having a transverse diameter slightly less than that of the cylindrical center portion. These novel caplet designs facilitate the dipping method herein provided since they are easily held by the above retaining means and can be manufactured using conventional compression molding equipment.

From the foregoing it can be realized that this invention provides a simulated capsule-like medicament, a method for manufacturing this medicament, and apparatus used in the method. The advantages over the prior art are: increased tamper-resistance over hollow capsules, increased swallowability over pan-coated medicaments, variable color scheme capability not available with pan-coated medicaments, less expensive operating costs and a greater perception by the consuming public that gelatin coated caplets are more effective. Although various embodiments have been illustrated, this was for the purpose of describing, but not limiting, the invention. Various modifications, which will become apparent to one skilled in the art, are within the scope of this invention described in the attached claims.

I claim:

1. An apparatus for coating a caplet with a gelatinous material to produce a capsule-like medicament comprising:
   (a) inserting means for inserting a first end of said caplet into a first holding means while leaving a second end of said caplet exposed;
   (b) said first holding means having at a first side a caplet channel defined therein for permitting the passage of said caplet, said holding means further comprising retaining means which is positioned near said first side to grip said caplet at a first end of said caplet and hold said caplet in position for application of a gelatinous coating to said second end;
   (c) first application means for applying a gelatinous coating to said second exposed end of said caplet including a bath of gelatinous material into which said second exposed end is moved while being held by said first holding means;
   (d) first drying means positioned after said first application means for permitting said second gelatinous coating to dry to form a coated second end;
   (e) gripping means which engages one end of said caplet for displacing said caplet through said caplet channel to expose said first end;
   (f) retaining means positioned adjacent one end of said holding means for retaining side caplet in said holding means with said first end exposed;
   (g) second application means for applying a gelatinous coating to said first end of said caplet including a bath of gelatinous material into which said first end is dipped while being held by said holding means;
   (h) dipping means positioned adjacent the bath of gelatinous material for moving said caplet ends into their respective bath of gelatinous material and removing the caplets from the bath once application is complete; and
   (i) second drying means positioned after said first application means for permitting said gelatinous coating on said first end to dry, forming a simulated capsule-like medicament.

2. The apparatus of claim 1 wherein said gripping means comprises transfer means for transferring said caplet from said first holding means to a second holding means.

3. The apparatus of claim 1 wherein said caplet channel comprises a cross-section sized to slidably mate with said caplet.

4. The apparatus of 2 wherein said first holding means comprises a central bore extending through its length to permit passage of said caplet through said bore.

5. The apparatus of claim 4 wherein said central bore comprises a transverse cross-section that is generally circular.

6. The apparatus of claim 4 wherein said transfer means comprises alignment means for aligning said first and second holding means during a displacement of said caplet from said first holding means to said second holding means.

7. The apparatus of claim 2 wherein said transfer means comprises plunging means for displacing said caplet through a portion of said caplet channel into a second holding means.

8. The apparatus of claim 2 wherein said second holding means comprises a central bore extending therethrough to permit passage of said caplet through said bore.

9. The apparatus of claim 8 wherein said second holding means comprises a second retaining means for retaining said caplet at least during coating.

10. The apparatus of claim 1 wherein said gelatinous coating comprises gelatin.

11. The apparatus of claim 4 wherein said inserting means comprises plunging means having an end portion disposed to abut said caplet to effect displacement into said bore of said first holding means.

12. The apparatus of claim 1 wherein said inserting means comprises a fixture comprising a plurality of holding means for receiving a multiple of caplets.

13. The apparatus of claim 12 wherein said inserting means further comprises plunging means having a plurality of end portions disposed to abut said multiple of caplets to effect displacement thereof into said fixture.

14. The apparatus of claim 12 wherein said fixture comprises a plurality of holding means mounted thereon.

15. The apparatus of claim 14 wherein said fixture comprises 10 to 50 holding means.

16. The apparatus of claim 15 wherein said fixture comprises 20 to 40 holding means.

17. The apparatus claim 14 wherein said holding means comprise cylindrical bores therein for gripping said caplets.

18. The apparatus of claim 17 wherein said bores extend through said holding means for passage therethrough of said caplets.

19. The apparatus of claim 1 wherein said dipping means comprises dipping means for vertically dipping said caplet into a bath of gelatinous material.

20. The apparatus of claim 1 wherein at least one of said first and second drying means (d) and (i) comprises rotating means for distributing said coating on said caplet.

21. The apparatus of claim 1 wherein at least one of said first and second drying means (d) and (i) comprises kiln means for drying said caplet.

22. The apparatus of claim 2 further comprising ejection means for removing said caplet from said second holder after said first end is dry.

23. The apparatus of claim 22 wherein said ejection means comprises an end portion disposed to abut said caplet to effect displacement of said caplet out of said second holding means.

* * * * *

UNITED STATES PATENT AND TRADEMARK OFFICE
CERTIFICATE OF CORRECTION

PATENT NO. : 5,314,537
DATED : May 24, 1994
INVENTOR(S) : Norbert I. Berta

It is certified that error appears in the above-indentified patent and that said Letters Patent is hereby corrected as shown below:

Column 11, Claim 1, Line 59, "retaining side caplet" should read -- retaining said caplet --.

Signed and Sealed this

Fifteenth Day of August, 1995

Attest:

BRUCE LEHMAN

Attesting Officer

Commissioner of Patents and Trademarks